US011400092B2

(12) United States Patent
Berry et al.

(10) Patent No.: US 11,400,092 B2
(45) Date of Patent: Aug. 2, 2022

(54) METHODS OF TREATING MYELOPROLIFERATIVE DISORDERS

(71) Applicant: Impact Biomedicines, Inc., Summit, NJ (US)

(72) Inventors: Tymara Berry, Morristown, NJ (US); John Hood, Del Mar, CA (US); Catriona Jamieson, La Jolla, CA (US); Curtis L. Scribner, Oakland, CA (US)

(73) Assignee: Impact Biomedicines, Inc., Summit, NJ (US)

( * ) Notice: Subject to any disclaimer, the term of this patent is extended or adjusted under 35 U.S.C. 154(b) by 0 days.

(21) Appl. No.: 17/560,373

(22) Filed: Dec. 23, 2021

(65) Prior Publication Data

US 2022/0133724 A1 May 5, 2022

Related U.S. Application Data

(63) Continuation of application No. 17/279,765, filed as application No. PCT/US2019/052608 on Sep. 24, 2019.

(60) Provisional application No. 62/783,076, filed on Dec. 20, 2018, provisional application No. 62/736,369, filed on Sep. 25, 2018.

(51) Int. Cl.
*A61K 31/51* (2006.01)
*A61P 35/02* (2006.01)
*A61K 31/675* (2006.01)

(52) U.S. Cl.
CPC .......... *A61K 31/51* (2013.01); *A61K 31/675* (2013.01); *A61P 35/02* (2018.01)

(58) Field of Classification Search
CPC .............. A61K 2300/00; A61K 31/506; A61K 31/519; A61K 31/635; A61P 35/00
See application file for complete search history.

(56) References Cited

U.S. PATENT DOCUMENTS

| | | |
|---|---|---|
| 7,528,143 B2 | 5/2009 | Noronha et al. |
| 7,825,246 B2 | 11/2010 | Noronha et al. |
| 8,133,900 B2 | 3/2012 | Hood et al. |
| 8,138,199 B2 | 3/2012 | Noronha et al. |
| 10,391,094 B2 | 8/2019 | Jayan et al. |
| 2007/0191405 A1 | 8/2007 | Noronha et al. |
| 2013/0102624 A1 | 4/2013 | Schloss |
| 2013/0243853 A1 | 9/2013 | Jayan et al. |
| 2014/0004516 A1 | 1/2014 | Sattler et al. |
| 2015/0148345 A1 | 5/2015 | Lannutti et al. |
| 2016/0332993 A1 | 11/2016 | Bradner et al. |
| 2019/0381041 A1 | 12/2019 | Jayan et al. |
| 2021/0244735 A1 | 8/2021 | Jayan et al. |
| 2022/0031699 A1 | 2/2022 | Berry et al. |
| 2022/0031713 A1 | 2/2022 | Gerike et al. |
| 2022/0133751 A1 | 5/2022 | Gerike et al. |

FOREIGN PATENT DOCUMENTS

| | | |
|---|---|---|
| WO | WO-2007/053452 A1 | 5/2007 |
| WO | WO-2012/061833 A1 | 5/2012 |
| WO | WO-2020/068754 A1 | 4/2020 |
| WO | WO-2020/068755 A1 | 4/2020 |
| WO | WO-2020/167844 A1 | 8/2020 |
| WO | WO-2020/167845 A1 | 8/2020 |

OTHER PUBLICATIONS

Jamieson et al. (Blood, 634. Myeloproliferative Syndromes: Clinical: Poster II | Nov. 15, 2013).*
ClinicalTrials.Gov, A Dose-Escalation Study of the Safety and Tolerability of Orally Administered TG101348 in Patients With Myelofibrosis, TargeGen, ClinicalTrials.gov Identifier: NCT00631462, 7 pages (last updated Oct. 22, 2009). URL: http://clinicaltrials.gov/ct2/show/study/NCT00631462 [Retrieved Jan. 10, 2011].
ClinicalTrials.Gov, A Long-Term Study of the Effects of Orally Administered TG101348 in Patients With Myelofibrosis, TargeGen, ClinicalTrials.gov Identifier: NCT00724334, 13 pages (last updated Dec. 9, 2009). URL: http://clinicaltrials.gov/ct2/show/study/NCT00724334 [Retrieved Jan. 10, 2011].
Curto-Garcia, N. et al., Thiamine deficiency appears uncommon in patients with Myeloproliferative Neoplasms, Brit. Jrnl. Haem., 178:327-340 (2017).
Curto-Garcia, N. et al., Thiamine deficiency appears uncommon in patients with Myeloproliferative Neoplasms, British Journal of Haematology, 178:327-340 (2017).
Giacomini, M.M. et al., Interaction of 2,4-Diaminopyrimidine-Containing Drugs Including Fedratinib and Trimethoprim with Thiamine Transporters (Correction), Drug Meta. Dispo., 1146-1147 (2017).
Giacomini, M.M. et al., Interaction of 2,4-Diaminopyrimidine-Containing Drugs Including Fedratinib and Trimethoprim with Thiamine Transporters, Drug Meta. Dispo., 45:76-85 (2017).
Harrison, et al., Janus kinase-2 inhibitor fedratinib in patients with myelofibrosis previously treated with ruxolitinib (JAKARTA-2): a single-arm, open-label, non-randomised, phase 2, multicentre study, The Lancet Haematology, 4(7): e317-e324 (2017).
Hazell, A.S. et al., Treatment of rats with the JAK-2 inhibitor fedratinib does not lead to experimental Wernicke's encephalopathy, Neurosci. Lett., 642:163-167 (2017).
Hood, J. et al., TG101348, A Potent, Highly Selective JAK2 Inhibitor, Inhibits Colony Formation in Stem Cells From Polycythemia Vera Patients and Prevents JAK2V617FMediated Splenomegaly and Death in a Mouse Model, 2007 ASCO Annual Meeting, Abstract 7031: 3 pages (2007). URL:http://www.asco.org/ascov2/Meetings/Abstracts?&vmview=abst_detail_view&confID=47 . . . [Retrieved Mar. 14, 2011].
International Search Report for PCT/US2019/052607, 5 pages (dated Dec. 12, 2019).
International Search Report for PCT/US2019/052608, 3 pages (dated Dec. 12, 2019).

(Continued)

*Primary Examiner* — Savitha M Rao
(74) *Attorney, Agent, or Firm* — Choate, Hall & Stewart LLP; Kristen C. Buteau; Michael A. Shinall

(57) ABSTRACT

The present disclosure provides methods of mitigating thiamine deficiency.

25 Claims, No Drawings

(56) References Cited

OTHER PUBLICATIONS

Lasho, et al., TG101348, a JAK2-selective antagonist, inhibits primary hematopoietic cells derived from myeloproliferative disorder patients with JAK2V617F, MPLW515K or JAK2 exon 12 mutations as well as mutation negative patients, Leukemia, 22: 1790-1792 (2008).
Mesa, R. A. et al., Emerging Drugs for the Therapy of Primary and Post Essential Thrombocythemia, Post Polycythemia Vera Myelofibrosis, Expert Opin. Emerg. Drugs, 14(3):471-479 (2009).
Pardanani, A. and Tefferi, A., Definition and management of ruxolitinib treatment failure in myelofibrosis, Blood Cancer Journal, 4: e268 1-7 (2014).
Pardanani, A. D. et al., A Phase I Evaluation of TG101348, a Selective JAK2 Inhibitor, in Myelofibrosis: Clinical Response is Accompanied by Significant Reduction in JAK2V617F Allele Burden, 51st ASH Annual Meeting and Exposition, Abstract No. 755: 2 pages (Dec. 7, 2009). URL: <http://ash.confex.com/ash/2009/webprogram/Paper20584.html> [Retrieved Nov. 29, 2010].
Pardanani, A. D. et al., A Phase I Study of TG101348, An Orally Bioavailable JAK2-Selective Inhibitor, in Patients With Myelofibrosis, 50th ASH Annual Meeting and Exposition, Abstract 97: 2 pages (Dec. 7, 2008). URL: <http://ash.confex.com/ash/2008/webprogram/Paper10141.html> [Retrieved Nov. 30, 2010].
Pardanani, A. et al. Safety and Efficacy of TG101348, A Selective JAK2 Inhibitor, in Myelofibrosis, J. Clin. Oncol. 29(7):789-796 (2011).
Pardanani, A. et al., A phase 2 randomized dose-ranging study of the JAK2-selective inhibitor fedratinib (SAR302503) in patients with myelofibrosis, Blood Can. Jrnl., 5(e335):1-8 (2015).
Pardanani, A. et al., Longer-Term Follow up With TG101348 Therapy in Myelofibrosis Confirms Sustained Improvement in Splenomegaly, Disease-Related Symptoms, and JAK2V617F Allele Burden, 52nd ASH Annual Meeting and Exposition, Abstract 459: 2 pages (Dec. 6, 2010). URL: <http://ash.confex.com/ash/2010/webprogram/Paper28895.html> [Retrieved Nov. 29, 2010].
Pardanani, A. et al., Safety and Efficacy of Fedratinib in Patients With Primary or Secondary Myelofibrosis: A Randomized Clinical Trial, JAMA Oncol, 1(5):643-51 (2015).
Pardanani, A. et al., TG101348, a JAK2-Selective Inhibitor, is Well Tolerated in Patients With Myelofibrosis and Shows Substantial Therapeutic Activity Accompanied by a Reduction in JAK2V617F Allele Burden, 14th Congress of the EHA, Berlin, Germany, Abstract 1088: 1 page (Jun. 4-7, 2009). URL: http://www.eventure-online.com/eventure/publicAbstractView.do?id=1027-69&congressId=2432. [Retrieved Nov. 30, 2010].
Polverelli, N. et al., Ruxolitinib- but not fedratinib-induced extreme thrombocytosis: the combination therapy with hydroxyurea and ruxolitinib is effective in reducing platelet count and splenomegaly/constitutional symptoms, Ann Hema., 94:1585-1587 (2015).
PubChem-CID: 16722836, pp. 1-27 (Create Date: Sep. 3, 2007).
Rodriguez-Pardo, J. et al., Putamina Involvement in Wenicke Encephalopathy Induced by Janus Kinase 2 Inhibitor, Clin. Neuropharm., 38(3):117-118 (2015).
Wernig, G. et al. Efficacy of TG101348, a Selective JAK2 Inhibitor, in Treatment of a Murine Model of JAK2V617F-Induced Polycythemia Vera, Cancer Cell, 13:311-320 (2008).
Written Opinion for PCT/US2019/052607, 8 pages (dated Dec. 12, 2019).
Written Opinion for PCT/US2019/052608, 10 pages (dated Dec. 12, 2019).
Zhang, Q. et al., The Janus Kineaase 2 Inhibitor Fedratinib Inhibits Thiamine Uptake: A Putative Mechanism for the Onset of Wernicke's Encephalopathy, Drug Meta. Dispo., 42:1656-1662 (2014).
Zhou, T. et al., Specificity and mechanism-of-action of the JAK2 tyrosine kinase inhibitors ruxolitinib and SAR302503 (TG101348), Leukemia (Correction), 28:471-472 (2014).
Zhou, T. et al., Specificity and mechanism-of-action of the JAK2 tyrosine kinase inhibitors ruxolitinib and SAR302503 (TG101348), Leukemia, 28:404-463 (2014).
Gunerka, P. et al., Differences in gene expression and alterations in cell cycle of acute myeloid leukemia cell lines after treatment with JAK inhibitors, European Journal of Pharmacology, 765:188-197 (2015).
Harrison, C. et al., Fedratinib in patients with myelofibrosis previously treated with ruxolitiinib: An updated analysis of the JAKARTA2 study using stringent criteria for ruxolitinib failure, American Journal of Hematology, 95(6):594-603 (2020).
Harrison, C. et al., Real-World Utilization of Febratinib for Myelofibrosis Post-Ruxolitinib: Patient Characteristics, Treatment Patterns, and Characterization of Ruxolitinib Failure, retreived from https://ash.confex.com/ash/2021/webprogram/Paper145569.html, 3 pages (2021).
Hood, J. and Hazell, A., Fedratinib Does Not Inhibit Thiamine Uptake or Induce Experimental Wernicke's Encephalopathy in Nonclincal Studies, Blood blood, 130:(Supp_1):4993, (2017).
Li, S. et al., Cancer gene profiling in non-small cell lung cancers reveals activating mutations in JAK2 and JAK3 with therapeutic implications, Genome Medicine, 9(89):1-11 (2017).
Mullally, A. et al., Fedratinib in meylofibrosis, Blood Advances, 4(8):1792-1800, (2020).
Passamonti, F. et al., Real-World Outcomes with Fedratinib Therapy in Patients Who Discontinued Ruxolitinib for Primary Myelofibrosis, retrieved from https://ash.confex.com/ash/202/webprogram/Paper148188.html, 2 pages (2021).
Talpaz, M. et al., A Phase II Randomized Dose-Ranging Study of the JAK2-Selective Inhibitor SAR302503 in Patients with Intermediate-2 or High-Risk Primary Myelofibrosis (MF), Post-Polycythemia Vera (PV) MF, or Post-Essential Thrombocythemia (ET) MF, Blood, American Society of Hematology, 120(21): 3 pages (2012).
Talpaz, M. et al., Fedratinib, a newly approved treatment for patients with myeloproliferative neoplasm-associated myelofibrosis, Leukemia, 35(1):1-17, (2021).

* cited by examiner

METHODS OF TREATING MYELOPROLIFERATIVE DISORDERS

CROSS-REFERENCE TO RELATED APPLICATIONS

The present application is a continuation application of U.S. patent application Ser. No. 17/279,765, filed Mar. 25, 2021, which is a 371 national phase application of PCT/US19/52608, filed Sep. 24, 2019, which claims priority to U.S. Provisional Patent Application Nos. 62/736,369, filed on Sep. 25, 2018, and 62/783,076, filed on Dec. 20, 2018, each of which is hereby incorporated by reference in its entirety.

FIELD OF THE INVENTION

The present invention provides methods of treating, stabilizing or lessening the severity or progression of a myeloproliferative disorder.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

The present disclosure provides methods of treating, stabilizing or lessening the severity or progression of one or more myeloproliferative disorders. In certain embodiments, provided methods comprise mitigating one or more adverse events associated with treatment of a myeloproliferative disorder. In some such embodiments, the one or more adverse event is a thiamine deficiency.

In some aspects, the present disclosure provides methods of treating, stabilizing or lessening the severity or progression of one or more myeloproliferative disorders comprising administering to a patient a pharmaceutically acceptable composition comprising a compound of formula I:

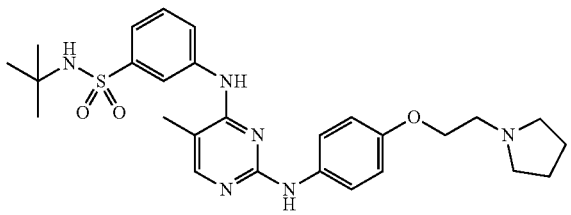

I or a pharmaceutically acceptable salt or hydrate thereof. The compound of formula I is also referred to herein as "Compound I". In some embodiments, Compound I is in the form of a dihydrochloride salt. Compound I, or a pharmaceutically acceptable salt thereof, may also exist in a hydrate form. In some such embodiments, Compound I is in the form of a dihydrochloride monohydrate. Accordingly, in some embodiments, provided methods comprise administering to a patient in need thereof Compound II:

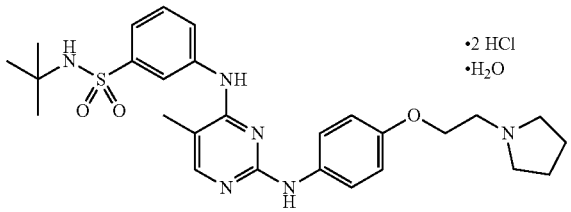

II

In some embodiments, the present disclosure provides a method of treating a myeloproliferative disorder, comprising
  (i) administering to a patient in need thereof Compound I, or a pharmaceutically acceptable salt or hydrate thereof, (e.g., Compound II); and
  (ii) monitoring the patient's thiamine levels;
wherein the patient's thiamine levels are adjusted if the level of thiamine is below a reference standard.

In some embodiments, the patient's thiamine levels are adjusted if the thiamine levels are about 10%, 15%, 20%, 25%, 30%, 35%, 40%, 45%, 50%, or more below a reference standard. In some embodiments, a reference standard is the patient's baseline level of thiamine prior to administration of Compound I. In some embodiments, a reference standard is a thiamine level that is from about 74 nM/L to about 222 nM/L of whole blood.

In some embodiments, the patient is at risk for developing Wernicke's encephalopathy.

In some embodiments, the patient's thiamine levels are assessed by analyzing one or more biomarkers for thiamine deficiency. In some embodiments, a biomarker for thiamine deficiency is a serum thiamine level.

In some embodiments, the patient's thiamine levels are adjusted by administering thiamine or a thiamine equivalent to the patient.

In some embodiments, the present disclosure provides a method for treating a patient comprising:
  (i) administering to the patient Compound I, or a pharmaceutically acceptable salt or hydrate thereof, (e.g., Compound II);
  (ii) analyzing the thiamine level in the patient; and
  (iii) administering to the patient thiamine or a thiamine equivalent if the patient's thiamine level is less than about 74 nM/L to about 222 nM/L of whole blood but greater than about 30 nM/L of whole blood.

In some embodiments, the patient is administered 100 mg thiamine per day. In some embodiments, the patient is administered a thiamine equivalent sufficient to deliver about 100 mg of thiamine per day. In some such embodiments, the thiamine or thiamine equivalent is administered orally.

In some embodiments, the present disclosure provides a method for treating a patient comprising:
  (i) administering to the patient Compound I, or a pharmaceutically acceptable salt or hydrate thereof, (e.g., Compound II);
  (ii) analyzing the thiamine level in the patient; and
  (iii) administering to the patient thiamine or a thiamine equivalent if the patient's thiamine level is less than or equal to about 30 nM/L of whole blood.

In some embodiments, the thiamine or thiamine equivalent is administered intravenously. In some embodiments, thiamine is administered to the patient at an amount of about 250 mg. In some embodiments, thiamine is administered to the patient at an amount of about 250 mg per day (QD). In some embodiments, the patient is administered a thiamine equivalent sufficient to deliver about 250 mg of thiamine per day.

In some embodiments, thiamine is administered to the patient at an amount of about 500 mg. In some embodiments, thiamine is administered to the patient at an amount of about 500 mg per day (QD). In some embodiments, the patient is administered a thiamine equivalent sufficient to deliver about 500 mg of thiamine QD. In some embodiments, thiamine is administered to the patient at an amount of about 500 mg three times daily (TID). In some embodiments, the patient is administered a thiamine equivalent sufficient to deliver about 500 mg of thiamine TID.

In some embodiments, thiamine is administered to the patient at an amount of about 500 mg TID for 2 or 3 days, followed by administration of thiamine at an amount of about 250 mg to about 500 mg daily (QD) for 3-5 days, followed by administration of thiamine at an amount of about 100 mg QD for 90 days.

In some embodiments, provided methods further comprise increasing the patient's magnesium level.

In some embodiments, the patient has a myeloproliferative disorder. In some such embodiments, the myeloproliferative disorder is myelofibrosis. In some embodiments, the myelofibrosis is primary myelofibrosis. In some embodiments, the primary myelofibrosis is Dynamic International Prognostic Scoring System (DIPSS) intermediate or high-risk primary myelofibrosis. In some embodiments, the myelofibrosis is secondary myelofibrosis. In some embodiments, the myelofibrosis is post-essential thrombocythemia myelofibrosis. In some embodiments, the myelofibrosis is post-polycythemia vera myelofibrosis. In some embodiments, the myeloproliferative disorder is polycythemia vera. In some embodiments, the myeloproliferative disorder is essential thrombocythemia. In some embodiments, the myeloproliferative disorder is acute myeloid leukemia (AML).

In some embodiments, the present disclosure provides a method for treating a patient comprising:
  (i) administering Compound I, or a pharmaceutically acceptable salt or hydrate thereof, (e.g., Compound II), and
  (ii) conducting a cognitive assessment.

In some embodiments, the cognitive assessment occurs during the $2^{nd}$ 28-day cycle. In some embodiments, the cognitive assessment occurs during the $3^{rd}$ 28-day cycle. In some embodiments, the cognitive assessment occurs during at least every $3^{rd}$ 28-day cycle. In some embodiments, the cognitive assessment comprises a mini-mental state examination. In some embodiments, the method further comprises analyzing thiamine level in the patient.

Definitions

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. As an example, when the term "about" is used in combination with a certain number of days, it includes said specific number of days plus or minus 1 day, e.g., "about 6 days" includes any number of days between 5 and 7. It is to be understood that the value to which the modifier "about" refers is itself also specifically, and preferably, disclosed.

The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

As used herein, the term "combination therapy" refers to situations in which a subject is simultaneously exposed to two or more therapeutic regimens (e.g., two or more therapeutic agents, including one or more compounds as described herein). The two or more regimens may be administered simultaneously or sequentially (e.g., all doses of a first regimen are administered prior to administration of any doses of a second regimen). In other embodiments, such compounds are administered in overlapping dosing regimens. "Administration" of a combination therapy may involve administration of one or more compounds to a subject receiving the other compound(s) in the combination. For clarity, combination therapy does not require that individual compounds be administered together in a single composition (or even necessarily at the same time or by the same route of administration), although in some embodiments, two or more compounds may be administered together in a combination composition, or even in a combination compound (e.g., as part of a single chemical complex or covalent entity).

The term "thiamine equivalent" refers to an agent that delivers or is capable of delivering a bioequivalent amount of thiamine. Such thiamine equivalents include prodrugs of thiamine as well as derivatives of thiamine such as thiamine monophosphate, thiamine pyrophosphate (also known as thiamine diphosphate), and thiamine triphosphate. In some embodiments, a thiamine equivalent is a dietary form of thiamine such as that found in vegetables or other food sources.

The terms "treat" or "treating," as used herein, refers to partially or completely alleviating, inhibiting, delaying onset of, preventing, ameliorating and/or relieving a disorder or condition, or one or more symptoms of the disorder or condition. As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

The expression "unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

DETAILED DESCRIPTION OF CERTAIN EMBODIMENTS

Myelofibrosis

Myeloproliferative neoplasm (MPN)-associated myelofibrosis (MF) is a serious and life-threatening disease that can present as a de novo or primary myelofibrosis (PMF) or evolve from previous polycythemia vera (post PV-MF) or essential thrombocythemia (post ET-MF) (Swerdlow S H, Campo E, Harris N L, Jafie E S, Pileri S A, Stein H, et al. World Health Organization classification of tumors of haematopoietic and lymphoid tissues. Lyon: IARC Press 2008). The disease is characterized by clonal myeloproliferation, ineffective erythropoiesis, bone marrow stromal changes, hepatosplenic extramedullary hematopoiesis, and aberrant cytokine expression (Tefferi A, Pardanani A. JAK inhibitors in myeloproliferative neoplasms: rationale, current data and perspective. Blood Rev. 2011 September; 25(5):229-37). Patients typically present with splenomegaly, constitutional symptoms, moderate to severe anemia, thrombocytopenia, and leukocytosis.

Primary myelofibrosis is a member of a group of Philadelphia chromosome (Ph1)-negative MPN which also includes PV and ET (Tefferi A. The recent advances in classic BCR-ABL-negative myeloproliferative disorders. Clin Adv Hematol Oncol. 2007a; 5:113-5). Almost all patients with PV and about one-half of patients with ET and PMF have a JAK2 mutation, typically JAK2V617F. Other mutations in patients with PMF include CALR and MPL. About 20% of patients with PMF have no detectable mutation in JAK2, CALR, or MPL and are termed triple negative (Levine R L, Wadleigh M, Cools J, Ebert B L, Wernig G, Huntly B J, et al. Activating mutation in the tyrosine kinase JAK2 in polycythemia vera, essential thrombocythemia, and myeloid metaplasia with myelofibrosis. Cancer Cell. 2005; 7:387-97; Werning G, Mercher T, Okabe R, Levine L, Lee B H, Gilliland G L. Expression of JAK2V617F causes a polycythemia vera-like disease with associated myelofibrosis in a murine bone marrow transplant model. Blood. 2006; 107:4274-81). Mutations in JAK2, CALR, and MPL result in activation of the JAK/STAT signaling pathway resulting in cell proliferation and inhibiting cell death. The result is clonal expansion (Ilhe J N, Gilliland D G. JAK2: normal function and role in hematopoietic disorders. Curr Opin Genet Dev. 2007; 17:8-14). Thus, a JAK2 inhibitor that can down regulate the JAK/STAT pathway is expected to be helpful in reducing cell proliferation.

Polycythemia vera (PV) and essential thrombocythemia (ET) are characterized by increased levels of red blood cells (RBC) and platelets. However, about 10% of affected patients develop bone marrow fibrosis morphologically indistinguishable from PMF. These conditions are termed post-PV-MF and post-ET-MF (Campbell P J, Green A R. Management of polycythemia vera and essential thrombocythemia. Hematology Am Soc Hematol Educ Program. 2005; 201-8), and are clinically named MPN associated myelofibrosis. Patients with MPN-associated myelofibrosis have similar survival prognoses to that of the PMF and about a 10% cumulative risk of transformation to acute myeloid leukemia (AML).

There are several prognostic scoring systems predicting survival of patients with PMF. The International Prognostic Scoring System (IPSS) is used to predict survival at diagnosis and the Dynamic International Prognostic Scoring System (DIPSS) at any time in the disease course (Cervantes F, Dupriez B, Pereira A, et al. New prognostic scoring system for primary myelofibrosis based on a study of the International Working Group for Myelofibrosis Research and Treatment. Blood. 2009; March 26; 113(13):2895-901; Passamonti F, Cervantes F, Vannucchi A M, Morra E, Rumi E, Pereira A, et al. A dynamic prognostic model to predict survival in primary myelofibrosis: a study by the IWG-MRT (International Working Group for Myeloproliferative Neoplasms Research and Treatment). Blood. 2010 Mar. 4; 115(9):1703-8). Variables included in the IPSS are age >65 years, constitutional symptoms, hemoglobin level <10 g/dL, and white blood cell (WBC) counts. Additional recent prognostic scoring systems include the Dynamic International Prognostic Scoring System Plus (DIPSS Plus) and scoring systems incorporating data from mutation analyses. There is a strong association between overall survival for MF patients and the DIPSS risk category for patients with low, intermediate risk 1, intermediate risk 2, or high risk with median survival of 15.4, 6.5, 2.9, and 1.3 years, respectively (Tefferi A. Primary myelofibrosis: 2017 update on diagnosis, risk-stratification, and management. Am J Hematol. 2016 December; 91(12):1262-1271).

Approximately 70% of individuals with MF are in the intermediate-2 or high-risk categories (Gangat N, Caramazza D, Vaidya R, George G, Begna K, Schwager S, et al. DIPSS plus: a refined Dynamic International Prognostic Scoring System for primary myelofibrosis that incorporates prognostic information from karyotype, platelet count, and transfusion status. J Clin Oncol. 2011 Feb. 1; 29(4):392-7), representing the greatest unmet medical need. Symptomatic enlargement of the spleen and liver, the necessity for RBC transfusions, cachexia, and the other MF-associated symptoms result in greatly compromised quality of life in these patients (Mesa R A, Camoriano J K, Geyer S M, Wu W, Kaufmann S H, Rivera C E, et al. A phase II trial of tipifarnib in myelofibrosis: primary, post-polycythemia vera and post-essential thrombocythemia. Leukemia. 2007 September; 21(9):1964-70).

Compound I

The synthesis of the Compound I is disclosed in Example 90 of U.S. Pat. No. 7,528,143, issued May 5, 2009, which is hereby incorporated by reference in its entirety. Compound I, also known as fedratinib, is a potent and selective inhibitor of JAK2 kinase activity that in cellular assays inhibits JAK2 signaling, cellular proliferation driven by mutant JAK2 or mutant MPL, and induces apoptosis in cells expressing constitutively active JAK2. Compound I also inhibits erythroid colony formation of hematopoietic progenitors isolated from myeloproliferative neoplasm (MPN) patients.

Myelofibrosis (MF) is a clonal disease resulting from mutations in CD34+ hematopoietic stem cells that promote abnormal proliferation and myeloid differentiation (Mead A J, 2017). In addition to JAK2V617F, several other mutations, in JAK2 and other genes, are found in MF patients and have been associated with prognosis, AML progression, and response to the JAK inhibitor ruxolitinib (Vainchenker W, Kralovics R. Genetic basis and molecular pathophysiology of classical myeloproliferative neoplasms. Blood. 2017 Feb. 9; 129(6):667-679, Tefferi A, Guglielmelli P, Nicolosi M, Mannelli F, et al. GIPSS: genetically inspired prognostic scoring system for primary myelofibrosis. Leukemia. 2018 Mar. 23; Spiegel J Y, McNamara C, Kennedy J A, Panzarella T, et al. Impact of genomic alterations on outcomes in myelofibrosis patients undergoing JAK1/2 inhibitor therapy. Blood. 2017 Sep. 8; 1(20):1729-1738; Newberry K J, Patel K, Masarova L, Luthra R, et al. Clonal evolution and outcomes in myelofibrosis after ruxolitinib discontinuation. Blood. 2017 Aug. 31; 130(9):1125-1131; Patel K P, Newberry K J, Luthra R, Jabbour E, et al. Correlation of mutation profile and response in patients with myelofibrosis treated with ruxolitinib. Blood. 2015 Aug. 6; 126(6):790-7; Levine R L, Wadleigh M, Cools J, Ebert B L, Wernig G, Huntly B J, et al. Activating mutation in the tyrosine kinase JAK2 in polycythemia vera, essential thrombocythemia, and myeloid metaplasia with myelofibrosis. Cancer Cell. 2005; 7:387-97; Werning G, Mercher T, Okabe R, Levine L, Lee B H, Gilliland G L. Expression of JAK2V617F causes a polycythemia vera-like disease with associated myelofibrosis in a murine bone marrow transplant model. Blood. 2006; 107:4274-81; Mercher T, Wernig G, Moore S A, Levine R L, Gu T L, Frohling S, Cullen D, Polakiewicz R D, Bernard O A, Boggon T J, Lee B H, Gilliland D G. JAK2T875N is a novel activating mutation that results in myeloproliferative disease with features of megakaryoblastic leukemia in a murine bone marrow transplantation model. Blood. 2006 Oct. 15; 108(8):2770-9; Scott L M, Tong W, Levine R L, Scott M A, Beer P A, Stratton M R, et al. JAK2 exon 12 mutations in polycythemia vera and idiopathic erythrocytosis. N Engl J Med. 2007 Feb. 1; 356(5):459-68; Pardanani A, Tefferi A, Jamieson C, Gabrail N Y, et al. A phase 2 randomized dose-ranging study of the JAK2-selective inhibitor fedratinib (SAR302503) in patients with myelofibrosis. Blood Cancer J. 2015 Aug. 7; 5:e335).

Phosphorylated STAT3 (pSTAT3) is a downstream effector of activated JAK2. Tracking pSTAT3 level in circulating cells has proven a useful pharmacodynamics (PD) biomarker of fedratinib-JAK2 engagement in MF patients (Pardanani A, Tefferi A, Jamieson C, Gabrail N Y, et al. A phase 2 randomized dose-ranging study of the JAK2-selective inhibitor fedratinib (SAR302503) in patients with myelofibrosis. Blood Cancer J. 2015 Aug. 7; 5:e335). Preclinical data indicates that fedratinib is also able to inhibit pSTAT5; and basal levels of pSTAT5 in AML cells have been reported to predict response to fedratinib in AML xenograft models (Chen W C, Yuan J S, Xing Y, Mitchell A, Mbong N, et al. An Integrated Analysis of Heterogeneous Drug Responses in Acute Myeloid Leukemia That Enables the Discovery of Predictive Biomarkers. Cancer Res. 2016 Mar. 1; 76(5): 1214-24). Abnormal cytokine expression and bone marrow fibrosis are hallmarks of MF (Vainchenker W, Kralovics R. Genetic basis and molecular pathophysiology of classical myeloproliferative neoplasms. Blood. 2017 Feb. 9; 129(6): 667-679; Mondet J, Hussein K, Mossuz P. Circulating Cytokine Levels as Markers of Inflammation in Philadelphia Negative Myeloproliferative Neoplasms: Diagnostic and Prognostic Interest. Mediators Inflamm. 2015; 2015: 670580). High levels of pro-inflammatory and fibrogenic cytokines have been reported to contribute to bone marrow (BM) stromal changes, ineffective erythropoiesis/extramedullary hematopoiesis and constitutional symptoms in MF (Mondet J, Hussein K, Mossuz P. Circulating Cytokine Levels as Markers of Inflammation in Philadelphia Negative Myeloproliferative Neoplasms: Diagnostic and Prognostic Interest. Mediators Inflamm. 2015; 2015:670580; Tefferi A, Pardanani A. JAK inhibitors in myeloproliferative neoplasms: rationale, current data and perspective. Blood Rev. 2011 September; 25(5):229-37). Fedratinib was found to modulate circulating cytokines in MF patients not previously treated with JAK inhibitors (Pardanani A, Tefferi A, Jamieson C, Gabrail N Y, et al. A phase 2 randomized dose-ranging study of the JAK2-selective inhibitor fedratinib (SAR302503) in patients with myelofibrosis. Blood Cancer J. 2015 Aug. 7; 5:e335). Cytokine modulation correlated with sustained viral response (SVR) and improvement in constitutional symptoms in these patients (Pardanani A, Tefferi A, Jamieson C, Gabrail N Y, et al. A phase 2 randomized dose-ranging study of the JAK2-selective inhibitor fedratinib (SAR302503) in patients with myelofibrosis. Blood Cancer J. 2015 Aug. 7; 5:e335).

Recent studies are starting to unveil immune regulatory roles for JAK2V617F, as well as for JAK inhibitors like ruxolitinib. For instance, JAK2V617F was found to contribute to immune evasion of MPN myeloid cells by upregulation of program death-ligand 1 (PD-L1) (Prestipino A, Emhardt A J, Aumann K, O'Sullivan D, et. al. Oncogenic JAK2V617F causes PD-L1 expression, mediating immune escape in myeloproliferative neoplasms. Sci Transl Med. 2018 Feb. 21; 10(429)), and ruxolitinib has been reported to modulate PD-L1 expression in these cells (Prestipino A, Emhardt A J, Aumann K, O'Sullivan D, et. al. Oncogenic JAK2V617F causes PD-L1 expression, mediating immune escape in myeloproliferative neoplasms. Sci Transl Med. 2018 Feb. 21; 10(429)). However, preclinical and clinical data indicate that ruxolitinib is also a potent immunosuppressive drug, which can suppress graft-versus-host disease (GVHD), decrease frequency and impair activation of T- and NK-cells of MF patients (Betts B C, Bastian D, Iamsawat S, Nguyen H, et al. Targeting JAK2 reduces GVHD and xenograft rejection through regulation of T cell differentiation. Proc Natl Acad Sci USA. 2018 Feb. 13; 115(7):1582-1587. Epub 2018; Schonberg K, Rudolph J, Vonnahme M, Parampalli et al. Cancer JAK Inhibition Impairs NK Cell Function in Myeloproliferative Neoplasms. Res. 2015 Jun. 1; 75(11):2187-99; Parampalli Yajnanarayana S, Stithig T, Cornez I, Alchalby H, et al. JAK1/2 inhibition impairs T cell function in vitro and in patients with myeloproliferative neoplasms. Br J Haematol. 2015 June; 169(6):824-33). Preclinical data suggest that fedratinib is able to modulate PD-L1 expression in lymphoma tumor cells (Hao Y, Chapuy B, Monti S, Sun H H, Rodig S J, Shipp M A. Selective JAK2 inhibition specifically decreases Hodgkin lymphoma and mediastinal large B-cell lymphoma growth in vitro and in vivo. Clin Cancer Res. 2014 May 15; 20(10):2674-83), however, it is neither a potent suppressor of GVHD, nor able to impair human T cell development in xenograft mouse models (Betts B C, Veerapathran A, Pidala J, Yang H, et al. Targeting Aurora kinase A and JAK2 prevents GVHD while maintaining Treg and antitumor CTL function. Sci Transl Med. 2017 Jan. 11; 9(372)). The selective activity of fedratinib on JAK2 raises the possibility that fedratinib might have immune-modulatory effects without impairing T- or NK-cell function in MF patients.

In some embodiments, the present disclosure provides a method for preventing and/or mitigating thiamine deficiency in a patient receiving Compound I, or a pharmaceutically acceptable salt or hydrate thereof, (e.g., Compound II). In some embodiments, the present disclosure provides a method for treating a patient comprising administering Compound I, or a pharmaceutically acceptable salt or hydrate thereof, (e.g., Compound II), and monitoring the thiamine levels in the patient.

In some embodiments, the present disclosure provides a method of treating a myeloproliferative disorder, comprising
(i) administering to a patient in need thereof a JAK1 and/or JAK2 inhibitor; and
(ii) monitoring the patient's thiamine levels.

In some such embodiments, the method further comprises adjusting the patient's thiamine levels if the level of thiamine is below a reference standard (e.g., baseline level). In some embodiments, the JAK1 and/or JAK2 inhibitor is Compound I, or a pharmaceutically acceptable salt thereof, (e.g., Compound II).

Accordingly, in some embodiments, the present disclosure provides a method of treating a myeloproliferative disorder, comprising
(i) administering to a patient in need thereof Compound I, or a pharmaceutically acceptable salt or hydrate thereof, (e.g., Compound II); and
(ii) monitoring the patient's thiamine levels;
wherein the patient's thiamine levels are adjusted if the level of thiamine is below a reference standard.

In some embodiments, the patient's thiamine levels are assessed by analyzing one or more biomarkers for thiamine deficiency. In some embodiments, a biomarker for thiamine deficiency is a serum thiamine level.

In some embodiments, the level of the biomarker is compared to a reference standard. In some embodiments, the reference standard is a baseline level of the biomarker (e.g., the level of the biomarker prior to administration of Compound I or Compound II). In some embodiments, the reference standard is a level of the biomarker that is considered to be within a range typically observed in a healthy population (e.g., a population that is not afflicted with the target disease or disorder). In some embodiments, the reference standard is a level of the biomarker that is considered to be within a range typically observed in a population that has been diagnosed with the target disease or disorder.

In some embodiments, the level of the biomarker following administration of Compound I or Compound II is lower than the reference standard (e.g., lower than the baseline level of the biomarker).

In some embodiments, the patient's thiamine levels are adjusted if the thiamine levels are about 10%, 15%, 20%, 25%, 30%, 35%, 40%, 45%, 50%, or more below a reference standard. In some embodiments, a reference standard is the patient's baseline level of thiamine prior to administration of Compound I or Compound II. In some embodiments, a reference standard is a thiamine level that is from about 74 nM/L to about 222 nM/L of whole blood.

In some embodiments, the patient is at risk for developing Wernicke's encephalopathy.

In some embodiments, the patient's thiamine levels are adjusted by administering thiamine or a thiamine equivalent to the patient.

In some embodiments, the present disclosure provides a method for treating a patient comprising:
(i) administering to the patient Compound I, or a pharmaceutically acceptable salt or hydrate thereof, (e.g., Compound II),
(ii) analyzing the thiamine level in the patient, and
(iii) administering to the patient thiamine or a thiamine equivalent if the patient's thiamine level is less than or equal to about 30 nM/L of whole blood.

In some embodiments, the present disclosure provides a method of mitigating thiamine deficiency, the method comprising administering Compound I, or a pharmaceutically acceptable salt or hydrate thereof, (e.g., Compound II), to a patient at risk for developing thiamine deficiency, wherein the patient is simultaneously exposed to thiamine or a thiamine equivalent.

In some such embodiments, the patient is administered about 100 mg thiamine per day. In some embodiments, the patient is administered a thiamine equivalent sufficient to deliver about 100 mg of thiamine per day. In some embodiments, the thiamine or thiamine equivalent is administered orally.

In some embodiments, the patient is administered a thiamine equivalent that delivers about 100 mg thiamine per day.

In some embodiments, the present disclosure provides a combination therapy comprising (i) Compound I, or a pharmaceutically acceptable salt or hydrate thereof, (e.g., Compound II), and (ii) thiamine or a thiamine equivalent.

In some embodiments, the present disclosure provides a method of treating myelofibrosis comprising administering to a patient in need thereof a combination therapy comprising Compound I, or a pharmaceutically acceptable salt or hydrate thereof, (e.g., Compound II), and thiamine or a thiamine equivalent. In some such embodiments, thiamine is administered in an amount of about 100 mg per day (QD). In some embodiments, the patient is administered a thiamine equivalent sufficient to deliver about 100 mg of thiamine per day. In some embodiments, the thiamine or thiamine equivalent is administered orally.

In some such embodiments, thiamine is administered in an amount of about 500 mg thiamine TID. In some such embodiments, the patient is administered about 250 or about 500 mg thiamine QD. In some embodiments, the patient is administered a thiamine equivalent sufficient to deliver about 250 mg or about 500 mg thiamine per day (QD). In some embodiments, the about 250 mg or about 500 mg thiamine is administered orally. In some embodiments, the thiamine equivalent is administered orally.

In some embodiments, a thiamine equivalent is thiamine pyrophosphate.

In some embodiments, provided methods further comprise increasing the patient's magnesium level. In some embodiments, the patient's magnesium level is increased by administering a magnesium supplement.

In some embodiments, the patient has a myeloproliferative disorder.

In some embodiments, the myeloproliferative disorder is myelofibrosis. In some embodiments, the myelofibrosis is primary myelofibrosis. In some embodiments, the myelofibrosis is secondary myelofibrosis. In some embodiments, the myelofibrosis is post-essential thrombocythemia myelofibrosis. In some embodiments, the myelofibrosis is post-polycythemia vera myelofibrosis.

In some embodiments, the myeloproliferative disorder is polycythemia vera. In some embodiments, the myeloproliferative disorder is essential thrombocythemia. In some embodiments, the myeloproliferative disorder is acute myeloid leukemia.

In some embodiments, Compound I is administered in the form of a dihydrochloride monohydrate (e.g., Compound II).

In some embodiments, Compound I, or a pharmaceutically acceptable salt or hydrate thereof, (e.g., Compound II), is administered to the patient in a unit dosage form. In some embodiments, the unit dosage form of Compound I or Compound II is based on the free base weight of the compound. For example, a 100 mg dose of the free base form of Compound I equates to about 117.30 mg of Compound I in its dihydrochloride monohydrate form (i.e., Compound II). In some embodiments, the unit dosage form of Compound I or Compound II is about 50 mg, about 100 mg, about 150 mg, or about 200 mg, based on the free base weight of the compound. In some embodiments, the unit dosage form of Compound I or Compound II is 100 mg, based on the free base weight of the compound.

In some embodiments, Compound I, or a pharmaceutically acceptable salt or hydrate thereof, (e.g., Compound II), is administered in an oral dosage form. In some such embodiments, the oral dosage form is a capsule. In some embodiments, the oral dosage form is a tablet.

In some embodiments, Compound I, or a pharmaceutically acceptable salt or hydrate thereof, (e.g., Compound II), is administered once daily (QD). In some embodiments, Compound I, or a pharmaceutically acceptable salt or hydrate thereof, (e.g., Compound II), is administered at a total daily dose of about 200 mg, about 300 mg or about 400 mg. In some embodiments, Compound I or Compound II is administered to the patient at a total daily dose of about 400 mg. In some embodiments, Compound I or Compound II is administered to the patient at a total daily dose of about 300 mg. In some embodiments, Compound I or Compound II is administered to the patient at a total daily dose of about 200 mg. In some embodiments, the total daily dose of Compound I or Compound II is modified due to an adverse event. In some embodiments, the total daily dose of Compound I or Compound II is reduced. In some embodiments, the total daily dose of Compound I or Compound II is reduced from about 400 mg to about 300 mg. In some embodiments, the total daily dose of Compound I or Compound II is reduced to about 200 mg.

In some embodiments, Compound I, or a pharmaceutically acceptable salt or hydrate thereof, (e.g., Compound II), is administered once daily for a 28 day cycle. In some embodiments, Compound I, or a pharmaceutically acceptable salt or hydrate thereof, (e.g., Compound II), is administered once daily for two 28-day cycles. In some embodiments, Compound I, or a pharmaceutically acceptable salt or hydrate thereof, (e.g., Compound II), is administered once daily for three, four, five, or more 28-day cycles. In some embodiments, Compound I, or a pharmaceutically acceptable salt or hydrate thereof, (e.g., Compound II), is administered once daily for six, seven, eight, nine, ten, eleven, twelve or more 28-day cycles. In some embodiments, Compound I, or a pharmaceutically acceptable salt or hydrate thereof, (e.g., Compound II), is administered once daily until symptoms of disease are no longer measureable. In some embodiments, Compound I or Compound II is administered for the duration of a patient's life. In some embodiments, Compound I or Compound II is administered once daily for one or more 28-day cycles, followed by a dose holiday. A "dose holiday" as used herein refers to a period of time wherein Compound I or Compound II is not administered to the patient. In some embodiments, a dose holiday is one day, one week, or one 28-day cycle. In some embodiments, Compound I or Compound II is administered once daily for one or more 28-day cycles, followed by a dose holiday, and then resumption of administration of Compound I or Compound II once daily at the same dose level prior to the dose holiday. In some embodiments, Compound I or Compound II is administered once daily for one or more 28-day cycles, followed by a dose holiday, and then resumption of administration of Compound I or Compound II once daily at a dose level that is 100 mg less than the dose of Compound I or Compound II prior to the dose holiday. In some embodiments, the total daily dose of Compound I or Compound II is titrated upward by 100 mg following a prior dose reduction.

In some embodiments, provided methods comprise administering Compound I, or a pharmaceutically acceptable salt or hydrate thereof, (e.g., Compound II), once daily for two or more 28-day cycles. In some such embodiments, the patient's thiamine levels are assessed at the beginning of the $2^{nd}$ 28-day cycle.

In some embodiments, provided methods comprise administering Compound I, or a pharmaceutically acceptable salt or hydrate thereof, (e.g., Compound II), once daily to the patient for two or more 28-day cycles, wherein the patient's thiamine levels are assessed at the beginning of every 28-day cycle. In some embodiments, provided methods comprise administering Compound I, or a pharmaceutically acceptable salt or hydrate thereof, (e.g., Compound II), once daily to the patient for two or more 28-day cycles, wherein the patient's thiamine levels are assessed at the end of each 28-day cycle. In some embodiments, provided methods comprise administering Compound I, or a pharmaceutically acceptable salt or hydrate thereof, (e.g., Compound II), once daily to the patient for two or more 28-day cycles, wherein the patient's thiamine levels are assessed at the beginning of the $2^{nd}$ 28-day cycle and at the beginning of the 3rd 28-day cycle. In some such embodiments, the patient's thiamine levels are assessed every $3^{rd}$ 28-day cycle thereafter. For example, if a patient is treated for twelve 28-day cycles, thiamine levels are assessed on day 1 (±3 days) of each of the $2^{nd}$ cycle, $3^{rd}$ cycle, $6^{th}$ cycle, $9^{th}$ cycle and $12^{th}$ cycle. In some embodiments, provided methods comprise administering Compound I, or a pharmaceutically acceptable salt or hydrate thereof, (e.g., Compound II), once daily to the patient for six or more 28-day cycles, wherein the patient's thiamine levels are assessed at the beginning of each of the $1^{st}$ cycle, $2^{nd}$ cycle, $3^{rd}$ cycle, $4^{th}$ cycle, $5^{th}$ cycle and $6^{th}$ cycle.

In some embodiments, provided methods comprise administering thiamine or a thiamine equivalent to the patient when the patient's thiamine levels are below normal (e.g., 74-222 nM/L of whole blood) but greater than or equal to 30 nM/L of whole blood. In some such embodiments, the thiamine or thiamine equivalent is administered orally. In some embodiments, thiamine is administered to the patient at a dose of about 100 mg per day. In some embodiments, the patient is administered a thiamine equivalent sufficient to deliver about 100 mg of thiamine per day.

In some embodiments, provided methods comprise administering thiamine or a thiamine equivalent when the patient's thiamine levels are 30 nM/L of whole blood. In some such embodiments, the thiamine is administered to the patient according to the following schedule:
  (i) about 500 mg three times daily (TID) for 2 or 3 days,
  (ii) about 250 mg to about 500 mg daily (QD) for 3 to 5 days, and
  (iii) about 100 mg daily (QD) for at least 90 days.

In some embodiments, a patient whose thiamine levels are 30 nM/L of whole blood is administered a thiamine equivalent sufficient to deliver an amount of thiamine according to the following schedule:
  (i) about 500 mg three times daily (TID) for 2 or 3 days,
  (ii) about 250 mg to about 500 mg daily (QD) for 3 to 5 days, and
  (iii) about 100 mg daily (QD) for at least 90 days.

In some embodiments, thiamine or thiamine equivalent is administered intravenously.

In some embodiments, provided methods further comprise monitoring the patient's magnesium levels. In some such embodiments, provided methods comprise increasing the patient's magnesium level.

In some embodiments, the patient has a myeloproliferative disease or condition. In some embodiments, the myeloproliferative disease or condition is selected from primary myelofibrosis, secondary myelofibrosis, polycythemia vera, essential thrombocythemia, post polycythemia vera, and post essential thrombocythemia. In some embodiments, the myeloproliferative disorder is acute myeloid leukemia (AML). In some embodiments, the primary myelofibrosis is Dynamic International Prognostic Scoring System (DIPSS) intermediate or high-risk primary myelofibrosis. In some embodiments, said method comprises administering to a patient in need thereof a composition according to the present invention.

In some embodiments, the present disclosure provides a method for treating a patient comprising:
  (i) administering Compound I, or a pharmaceutically acceptable salt or hydrate thereof, (e.g., Compound II), and
  (ii) conducting a cognitive assessment.

In some embodiments, the cognitive assessment occurs during the $2^{nd}$ 28-day cycle. In some embodiments, the cognitive assessment occurs during the $3^{rd}$ 28-day cycle. In some embodiments, the cognitive assessment occurs during at least every $3^{rd}$ 28-day cycle. In some embodiments, the cognitive assessment comprises a mini-mental state examination. In some embodiments, the method further comprises analyzing thiamine level in the patient.

EXEMPLIFICATION

Protocol Summary. A multicenter, single-arm, open-label efficacy and safety study of fedratinib in subjects previously treated with ruxolitinib and with DIPSS (Dynamic International Prognostic Scoring System) intermediate or high-risk primary myelofibrosis (PMF), post-polycythemia vera myelofibrosis (post-PV MF), or post-essential thrombocythemia myelofibrosis (post-ET MF).

Objectives. The primary objective of the study is to evaluate the percentage of subjects with at least a 35% spleen volume reduction with fedratinib. The secondary objectives are:
  To evaluate the safety of fedratinib
  To evaluate the reduction of spleen size by palpation
  To evaluate myelofibrosis (MF)-associated symptoms as measured by the Myelofibrosis Symptom Assessment Form (MFSAF)
  To evaluate duration of spleen response by MRI (magnetic resonance imaging)/CT (computed tomography) and by palpation
  To evaluate the duration of symptoms response
  To assess the effectiveness of the risk mitigation strategy for gastrointestinal (GI) events
  To assess the risk mitigation strategy for Wernicke's encephalopathy (WE)

The exploratory objectives are:
  To evaluate Overall Survival (OS)
  To assess the effect of study treatment on selected treatment-related symptoms from the subject's perspective (diarrhea, nausea, vomiting, dizziness, headache), assessed by the Patient Reported Outcome Version of the Common Terminology Criteria for Adverse Events (PRO-CTCAE)
  To explore prognostic markers (e.g., gene mutations, cytogenics) at baseline and in relation to efficacy parameters
  To explore biomarkers related to mechanisms of action of fedratinib (eg, circulating cytokines)

Study Population. The study will enroll approximately 110 subjects with intermediate- or high-risk primary myelofibrosis (PMF), post-polycythemia vera myelofibrosis (post-PV MF), or post-essential thrombocythemia myelofibrosis (post-ET MF).

All subjects discontinued from protocol-prescribed therapy for any reason will be followed for survival, subsequent therapies, and progression of myelofibrosis to acute myeloid leukemia (AML) every 3 months until death or up to 12 months after End of Treatment (EOT), lost to follow-up, withdrawal of consent for further data collection, or study closure, whichever comes first.

Study Design. The study will consist of the following 3 phases:

A 28-day Screening Period

Fedratinib Treatment Period including a 30-Day Follow-up After Last Dose Visit

A 12 month Survival Follow-up Period

Length of Study. The expected duration of study is approximately 4 years, which includes approximately 18 months to fully enroll, and 24 months for treatment and follow-up.

The End of Trial is defined as either the date of the last visit of the last subject to complete the Survival Follow-up, or the date of receipt of the last data point from the last subject that is required for primary, secondary and/or exploratory analysis, as prespecified in the protocol, whichever is the later date.

Screening Period. All enrolled subjects will undergo screening procedures during the screening period which must be completed within 28 days prior to the start of study treatment. This will serve to determine subject eligibility based on all inclusion and exclusion criteria defined in the protocol. For subjects that are receiving ruxolitinib during the screening period or that have potentially reversible laboratory abnormalities (or other criteria that excludes the subject from enrollment) detected during screening, the screening period may be extended to 35 days (additional 7 days).

Treatment Period. Upon confirmation of eligibility, subjects will be enrolled and receive treatment with fedratinib at a dose of 400 mg once daily orally continuously. Fedratinib is administered as the dihydrochloride monohydrate form (i.e., Compound II). Cycles are defined for administrative purposes as 4-week (28-day) periods. Unless otherwise noted, visit windows are ±3 days except for MRI/CT scan procedures which have a visit window of ±7 days. For the first 3 cycles, site visits will be performed on Day 1 and Day 15 and thereafter on Day 1 for the subsequent cycles. At Cycle 1 Day 8 the site will contact the subject by telephone to assess occurrence and discuss management of nausea, vomiting and diarrhea. Subjects may continue treatment with fedratinib until unacceptable toxicity, lack of therapeutic effect or withdraws consent. All subjects will be monitored for adverse events during the study. All subjects discontinued from protocol prescribed therapy for any reason will be followed for a period of 30 days following the last dose of fedratinib.

Fedratinib is self-administered orally once daily continuously on an outpatient basis, preferably together with food at dinner in the evening, the same time each day. In case a dose is missed, the next dose should be taken the following day at the same time of day as previously taken before the dose was missed.

For the first 3 cycles, site visits will be performed on Day 1 and Day 15 and thereafter on Day 1 for the subsequent cycles. At Cycle 1 Day 8 the site will contact the subject by telephone to assess occurrence and discuss management of nausea, vomiting and diarrhea.

Subjects may continue treatment with fedratinib until unacceptable toxicity, lack of therapeutic effect, progression of disease, or until consent is withdrawn.

All subjects will be monitored for adverse events during the study.

All subjects discontinued from protocol-prescribed therapy for any reason will be followed for at least a period of 30 days following the last dose of fedratinib.

The most common adverse events associated with fedratinib are hematological and gastrointestinal. Hematological adverse events associated with JAK inhibitors are dose dependent, mechanism-based and their managed through dose reductions, dose interruptions and transfusions.

The fedratinib dose in this study is 400 mg/day. If a subject experience a drug toxicity as specified in the Dose Modification Schedule table (Table 1), the dosing should be interrupted and the dose may need to be modified.

If a subject does not tolerate fedratinib therapy after 2 dose level reductions from the starting dose, he/she must be withdrawn from the study treatment. If the toxicity does not resolve in the time period as specified in the Dose Modification Schedule table (Table 1), subjects must be withdrawn from the study treatment. Reescalation of doses is possible in certain cases as defined in the Dose Modification Schedule table (Table 1). The daily dose of fedratinib cannot exceed 400 mg/day.

Subjects may continue treatment with fedratinib until unacceptable toxicity, lack of therapeutic effect or until a subject is not compliant with treatment or withdraws consent.

Dose Modification Schedule

A flexible dose modification regimen may be employed to minimize drug toxicity for individual subjects, with possible daily doses are of 200 mg, 300 mg, or 400 mg.

The most common adverse events associated with fedratinib are hematological and gastrointestinal events. Hematological adverse events associated with JAK inhibitors are dose dependent, mechanism-based and are managed through dose reductions, dose interruptions and transfusions.

If a subject experiences a drug toxicity as specified in Table 1, infra, the dosing must be interrupted; in some cases (i.e. when it is not a liver function test (LFT) abnormality) the dose can be titrated by a 100 mg/day decrement during the study, depending upon the Investigator's judgment, down to a minimum dose of 200 mg/day. For subjects with severe impairment of renal function and co-administration of strong or moderate CYP3A4 inhibitors the fedratinib dose is adjusted.

If a subject does not tolerate fedratinib therapy after 2 dose level reductions from the starting dose, he/she must be withdrawn from the study treatment. If the toxicity does not resolve in the time period as specified in Table 1, subjects must be withdrawn from the study treatment. Reescalation of doses is possible in certain cases. The daily dose of fedratinib cannot exceed 400 mg/day (based on the free base weight).

TABLE 1

| Dose Modification Schedule | | | |
| --- | --- | --- | --- |
| Adverse Event | Fedratinib Management | Recovery | Fedratinib Dose After Recovery |
| Hematological | | | |
| Grade 4 or Grade 3 thrombocytopenia with major bleeding | Hold fedratinib up to 28 days | Grade ≤3 thrombocytopenia without bleeding | Dose decrement by 1 dose level: 100 mg/daily decrease |
| Grade 4 neutropenia | Hold fedratinib up to 28 days | Grade ≤2 neutropenia | Dose decrement by 1 dose level: 100 mg/daily decrease |

TABLE 1-continued

Dose Modification Schedule

| Adverse Event | Fedratinib Management | Recovery | Fedratinib Dose After Recovery |
|---|---|---|---|
| Grade 4 hematological toxicity with dose reduction in subsequent cycle | — | Toxicity resolves for at least 1 cycle | Subsequent upward dose titration possible of 1 dose level (100 mg daily) per cycle as per the Investigator's discretion |
| Recurrence of a grade 4 hematological toxicity | — | — | Subsequent upward dose titration not permitted Fedratinib discontinuation as per the Investigator's discretion |
| Non-hematological | | | |
| Drug-related non-hematological Grade 4 or unmanageable Grade 3 toxicity with dose reduction in subsequent cycle | — | — | Subsequent upward dose titration not permitted Fedratinib discontinuation as per the Investigator's discretion |
| Hepatic (LFT abnormalities) | | | |
| Grade ≥3 AST or ALT or total bilirubin | Hold fedratinib Weekly monitoring of LFTs, until resolution, After fedratinib resumed, LFT monitoring every 2 weeks for the 3 subsequent cycles at a minimum | Grade ≤1 | Fedratinib Hold ≤14 days: Dose decrement by 1 dose level: 100 mg daily decrease Subsequent upward dose titration not permitted Fedratinib Hold >14 days (AE did not return to Grade ≤1): fedratinib permanently discontinued Grade 4 in the absence of demonstrable cause: permanently discontinue fedratinib |
| Recurrence of LFT abnormality (i.e. ≥Grade 3 toxicity) after dose reduction | Discontinue fedratinib permanently | — | — |
| Gastrointestinal | | | |
| Grade 2 nausea, vomiting, diarrhea, or constipation that does not respond to adequate therapeutic or supportive measures within 48 hours | Hold fedratinib up to 14 days | Toxicity resolves to Grade ≤1 | Consider resuming the dose at the same level after resolution of adverse event |
| Grade ≥3 or recurrence of Grade 2 nausea vomiting, diarrhea, or constipation that does not respond to adequate therapeutic or supportive measures within 48 hours | Hold fedratinib up to 14 days | Toxicity resolves to Grade ≤1 | Consider reducing one dose level after resolution of adverse event |
| Other Adverse Events Not Described Above | | | |
| Grade ≥3 or recurrence of Grade 2 that does not respond to adequate therapeutic or supportive measures within 48 hours | Hold fedratinib up to 14 days | Toxicity resolves to Grade ≤1 | Consider reducing one dose level after resolution of adverse event |

TABLE 1-continued

Dose Modification Schedule

| Adverse Event | Fedratinib Management | Recovery | Fedratinib Dose After Recovery |
|---|---|---|---|
| Grade ≥3 non-hematological toxicity, non-gastrointestinal toxicity or Grade ≥2 peripheral neuropathies | Hold fedratinib up to 14 days | Toxicity resolved to Grade ≤1 | Dose decrement by 1 dose level: 100 mg daily decrease |

Dose Adjustment for Co-Administration with Strong and Moderate CYP3A4 Inhibitors Concomitant administration of fedratinib with strong or moderate CYP3A4 inhibitors can increase fedratinib exposure. Increased fedratinib exposure may increase the risk of exposure-related AEs and need to be considered carefully.

For subjects with a co-administration of a strong CYP3A4 inhibitor a dose reduction of the starting dose of fedratinib from 400 mg to 200 mg is recommended. In case a strong CYP3A4 inhibitor is required to be introduced during fedratinib treatment consider dose reduction by 2 decrement dose level (e.g. 300 mg to 100 mg). Strong CYP3A4 inhibitors include, but are not limited to, boceprevir, cobicistat, conivaptan, danoprevir and ritonavir, elvitegravir and ritonavir, grapefruit juice, indinavir and ritonavir, itraconazole, ketoconazole, lopinavir and ritonavir, paritaprevir and ritonavir and (ombitasvir and/or dasabuvir), posaconazole, ritonavir, saquinavir and ritonavir, telaprevir, tipranavir and ritonavir, troleandomycin, and voriconazole.

For subjects with a co-administration of a moderate CYP3A4 inhibitor a dose reduction from the starting dose of fedratinib from 400 mg to 300 mg is recommended. In case a moderate CYP3A4 inhibitor is required to be introduced during fedratinib treatment consider dose reduction by 1 decrement dose level (e.g. 300 mg to 200 mg). Moderate CYP3A4 inhibitors include, but are not limited to, aprepitant, cimetidine, ciprofloxacin, clotrimazole, crizotinib, cyclosporine, dronedarone, erythromycin, fluconazole, fluvoxamine, imatinib, tofisopam, and verapamil.

If the fedratinib dose needs to be reduced below 100 mg daily based on any fedratinib related AEs due to a potentially increased plasma concentration of fedratinib, consider a lower average daily dose by administering, for example, 100 mg fedratinib every other day that is equivalent to an average daily dose of 50 mg.

If AEs are still not resolved after reducing fedratinib dose, consider interrupting dosing of either fedratinib or strong CYP3A4 inhibitors based on overall benefit/risk for a patient.

In cases where co-administration with the CYP3A4 inhibitor is discontinued, the fedratinib dose should be re-escalated accordingly.

Dose adjustment for renal impairment. No dose adjustment is recommended in subjects with mild and moderate renal impairment. In subjects that develop severe renal impairment during the study the fedratinib dose should be adjusted by one dose decrement level (e.g. from 400 mg to 300 mg once a day [QD]). Subject on a planned dose of 200 mg QD are allowed to reduce to 100 mg.

Management of Potential Wernicke's Encephalopathy (WE)

A potential case of WE is a medical emergency. Screening for WE and management of potential cases of WE during treatment with fedratinib will be done according the following steps:

Clinical and Cognitive Assessment. Interval history: including a review of the subject's history for confusion, memory problems, vision problems (e.g. double vision) as well as poor nutrition, signs and symptoms of malabsorption, and alcohol use Physical examination: including assessment for abnormal eye movements, cerebellar abnormalities and body weight (weight loss compared to previous examination or patient history) during screening and Day 1 of every treatment cycle, at the End of Treatment (EOT), and the 30-Day Follow-up visit Mini-Mental State Examination (MMSE): to objectively assess for signs/symptoms of encephalopathy during screening, on Day 1 of Cycles 2 and 3 and every third cycle thereafter, at EOT, and more frequently as clinically indicated Management of Potential WE. In case of signs or symptoms that may indicate WE:

Hold fedratinib until WE is ruled out
Obtain sample for thiamine level
Empirically start thiamine supplementation
Report the event as an AESI to the Sponsor
Obtain a neurological consult
Perform a brain MRI
If WE is confirmed discontinue fedratinib permanently Thiamine Monitoring and Correction. Thiamine levels (for whole blood) will be monitored and thiamine supplementation will be administered to all subjects with thiamine levels below the normal range.

Thiamine levels are assessed at screening and need to be corrected and retested before starting fedratinib treatment While on treatment with fedratinib, thiamine levels are assessed at start of Cycle 2, 3 and every third cycle thereafter or as clinically indicated:

If a subject is on thiamine supplementation, thiamine levels should be assessed in a fasting state for thiamine supplementation and thiamine given after the blood draw If a thiamine level result is below normal, the site will contact the subject as soon as possible to start thiamine supplementation For thiamine levels below the normal range but ≥30 nM/L without signs or symptoms of WE:

Supplementation with 100 mg oral thiamine must be started

If the results were obtained by a local laboratory, report the event as an Adverse Event of Special Interest (AESI) to the Sponsor For thiamine level <30 nM/L with or without signs or symptoms of WE:
  Immediate treatment with thiamine (preferably intravenous (IV)) at therapeutic dosages (e.g., 500 mg infused over 30 minutes 3 times daily for 2 to 3 days) or alternatively intramuscular (IM) in equivalent doses according to local standard of care
  Report the event as an Adverse Event of Special Interest (AESI) to the Sponsor
  This will be followed by 250 mg to 500 mg IV thiamine infused once a day for 3 to 5 days or alternatively IM in equivalent doses according to local standard of care
  And then continue at an oral daily dose of 100 mg thiamine for at least 90 days
  Fedratinib must be held until thiamine levels are restored to normal range.
Thiamine supplementation should be administered as a thiamine only formulation.
If thiamine levels are low, ensure that magnesium levels are normal or corrected if low
An Adverse event of special interest (AESI) is one of scientific and medical interest specific to understanding of the Investigational Product and may require close monitoring and rapid communication by the Investigator to the sponsor.
The following are considered to be Adverse Events of Special Interest (AESI):
  Wernicke's encephalopathy (WE) or suspected cases of WE associated with thiamine levels below normal range.
  Thiamine levels below normal range with or without signs or symptoms of WE
  New malignancy after start of study treatment
  Progression of myelofibrosis to acute myeloid leukemia (AML)
  Cardiac failure or cardiomegaly
  Grade 3 and 4 hyperlipasemia or Grade 3 and 4 hyperamylasemia according to CTCAE criteria, v 5.0 or events of pancreatitis
  Grade 3 or 4 alanine transaminase (ALT), aspartate transaminase (AST), or total bilirubin elevation or events of hepatotoxicity
Management of Nausea and Vomiting. Management of nausea and vomiting during treatment with fedratinib will be done according the following steps:
  Subjects will be provided management instructions (including when to contact the study site) before the start of treatment
  In order to mitigate for nausea and vomiting events, it is recommended to take fedratinib with food during an evening meal.
  It is highly recommended to use anti-nausea/vomiting treatment prophylactically according to local practice for the first 8 weeks of treatment (e.g., ondansetron). If dimenhydrinate or other muscarinic receptor antagonists are used for nausea and vomiting, administer these agents in the evening to minimize drowsiness and other potential neurological AEs
  Hold/reduce the dose of fedratinib according to Table 1
  Hospitalization may be indicated for Grade 3 or higher nausea or vomiting or events that persist
  For medications that are administered for prophylactic use of nausea and vomiting, if no clinically significant nausea and vomiting occurs during the first 8 weeks of fedratinib treatment, consider weaning the subject off these medications Management of Diarrhea. Management of diarrhea during treatment with fedratinib will be done according the following steps:
  Subjects should have loperamide available at home and should be provided with diarrhea management instructions (including when to contact the study site) before the start of treatment
  Loperamide should not be given as prevention in case the subject does not experience diarrhea
  Treat with loperamide as per local practice at the onset of diarrhea. Consider starting loperamide at a 4 mg loading dose and then 2 mg after each diarrheal bowel movement without exceeding 16 mg/24 hours
  Dietary modifications including adequate hydration, avoidance of lactose containing foods and alcohol, small meals with rice, bananas, bread, etc.
  Hold/reduce the dose of fedratinib according to Table 1
  Hospitalization may be indicated for Grade 3 or higher persisting diarrhea.
  Management of nausea, vomiting and diarrhea will be assessed during the subject's visit on Day 1 of every following 28-day cycle, at Day 15 of the first three cycles and by a mandatory telephone contact at Day 8 of the first cycle.
Overview of Key Efficacy Assessments
Unless otherwise specified, analysis of spleen volume response will be performed on the efficacy evaluable population, myelofibrosis symptom response analyses will be performed on the MFSAF population and spleen size response analyses will be performed on the safety population.
Spleen Volume Response Rate (RR) by MRI/CT. Response rate of reduction in spleen volume is defined as proportion of subjects who have a ≥35% reduction in spleen volume at the end of Cycle 6 as compared to baseline. The response rate and 95% confidence interval will be provided. In addition, a descriptive summary of spleen volumes measurements and percentage change from baseline will be provided. Subjects with a missing MRI/CT spleen volume at the end of Cycle 6 including those who meet the criteria for progression of splenomegaly before the end of Cycle 6 will be considered non-responders.
A sensitivity analysis will be conducted for response rate of subjects who have a ≥25% reduction in spleen volume at the end of Cycle 6 as compared to baseline.
Spleen Response Rate by Palpation (RRP). Spleen response rate by palpation is the proportion of subjects with a spleen response according to the IWG-MRT 2013 at the end of Cycle 6 as compared to baseline. This will be calculated for subjects that have an enlarged spleen (≥5 cm below LCM) at baseline. Subjects with a missing spleen size assessment at the end of Cycle 6 including those who meet the criteria for progression of splenomegaly before the end of Cycle 6 will be considered not to be responders. The response rate and 95% confidence interval will be provided.
Symptom Response Rate (SRR). Symptom response rate (SRR) is defined as the proportion of subjects with ≥50% reduction from baseline to the end of Cycle 6 in total symptom score (TSS) measured by MFSAF version 4.0. The SRR and 95% confidence interval will be provided. The TSS will be defined as the sum of each of the 7 symptom scores (Gwaltney C, Paty J, Kwitkowski V E, Mesa R A, Dueck A C, Papadopoulos E J, et al. Development of a harmonized patient-reported outcome questionnaire to assess myelofibrosis symptoms in clinical trials. Leuk Res. 2017 August; 59:26-31). To allow indirect comparison with previous MF studies, a modified TSS (Mesa R A, Gotlib J, Gupta V, Catalano J V, Deininger M W, Shields A L, et al. Effect of ruxolitinib therapy on myelofibrosis-related symptoms and other patient-reported outcomes in COMFORT-I: a randomized, double-blind, placebo-controlled trial. J Clin Oncol. 2013 Apr. 1; 31(10):1285-92) will also be derived from the 6 symptoms considered (night sweats, pruritus, abdominal discomfort, early satiety, pain under ribs on left side, bone or muscle pain) and analysis of SRR will be also performed.

At each timepoint, the TSS (based on 7 symptoms) and the modified TSS will be calculated. Descriptive summary statistics (size, mean, standard deviation, median, range) will be provided for baseline scores, postbaseline scores and change from baseline for TSS, modified TSS and symptom scores.

Subjects without a baseline TSS>0 will be considered non-evaluable (due to no place for symptom reduction) for the SRR analysis. Subjects with a missing TSS at the end of Cycle 6 or who had disease progression before the end of the Cycle 6 will be considered non-responders.

Duration of Spleen Volume Response by MRI/CT (DR). Duration of spleen volume response (DR) by MRI/CT is defined as time from the first documented spleen response (ie, ≥35% reduction in spleen volume) to the first documented spleen volume reduction <35%. In the absence an event (ie subsequent spleen volume reduction <35% before the analysis is performed), the DR will be censored at the date of the last valid assessment performed before the analysis performed date.

Duration of spleen volume response by MRI/CT scan will be analyzed using Kaplan-Meier method. K-M estimates of the 25th, 50th, and 75th percentiles and the 95% confidence interval of median will be provided. K-M curves will be plotted.

Duration of Spleen Response by Palpation (DRP). Duration of spleen response by palpation (DRP) is defined as time from the first documented palpable spleen response, according to the IWG-MRT 2013 to the time of the first documented loss of response according to the IWG-MRT 2013. Duration of spleen response by palpation according to the IWG-MRT 2013 criteria will be calculated for subjects that have an enlarged spleen at baseline (≥5 cm below LCM), and that have a spleen response by palpation. In the absence of an event (ie no loss of spleen response by palpation) before the analysis is performed, the DRP will be censored at the date of the last valid assessment performed before the analysis performed date.

Duration of Symptoms Response (DSR). Duration of symptoms response is defined as time from the first documented response in TSS (ie, reduction in TSS≥50%) measured by MFSAF version 4.0 to the first documented TSS reduction <50%. In the absence of TSS reduction <50% before the analysis performed, the DSR will be censored at the date of the last valid assessment performed before the analysis performed date. DRS will be analyzed using K-M method. The K-M estimates of the 25th, 50th, and 75th percentiles and the 95% confidence intervals of median will be provided, and K-M curves will be plotted.

TABLE 2

Study Endpoints

| Endpoint | Name | Description | Timeframe |
|---|---|---|---|
| Primary | Spleen volume response rate | Proportion of subjects who have a ≥35% reduction in spleen volume at the end of Cycle 6 | From Screening to the end of Cycle 6 |
| Secondary | Safety profile of fedratinib | Incidence and severity of all Grade adverse events (AEs) per NCI CTC Incidence and severity of Grade 3-4 AEs as per the NCI CTC, including laboratory parameters | From ICF signature up until 30 days post last dose For fedratinib related AEs, anytime until the last study visit |
| | Spleen response rate by palpation | Proportion of subjects who have a ≥50% reduction in spleen size by palpation | From C1D1 to the end of cycle 6 |
| | Symptom response rate | Proportion of subjects with a ≥50% reduction in total symptom scores measured by MFSAF | From C1D1 to the end of cycle 6 |
| | Durability of spleen response | Duration of ≥35% reduction in spleen volume | From screening to the End of Treatment visit |
| | Durability of spleen response by palpation | Duration of ≥50% reduction in spleen size by palpation for subjects with a palpable spleen at least 5 cm below the left costal margin (LCM) at C1D1 | From C1D1 until the 30-day follow-up after last dose visit |
| | Durability of symptoms response | Duration of ≥50% reduction in total symptom scores measured by MFSAF | From C1D1 until the 30-day follow-up after last dose visit |
| | Assessment of risk mitigation strategy for gastrointestinal adverse events and potential Wernicke's encephalopathy (WE) | Incidence of patients with a CTCAE grade ≥3 of nausea, diarrhea, or vomiting, or occurrence of WE (confirmed by brain MRI or autopsy). Assessment of thiamine levels at screening, on Day 1 of the first 3 cycles and every third cycle thereafter, and at the End of Treatment visit | From ICF signature to the 30-day follow-up after last dose visit |

TABLE 2-continued

Study Endpoints

| Endpoint | Name | Description | Timeframe |
|---|---|---|---|
| | HRQoL measured by EORTC QOL-C30 domains | Mean changes in the HRQoL function and symptom domain scores over the study compared with C1D1 | From C1D1 to Day 1 of each cycle, at the End of Treatment visit up to the 30-day follow-up after last dose visit |
| | PRO measured by EQ-5D-5L | Mean changes in the health utility scores over the study compared with enrollment measured by EQ-5D-5L | From C1D1 to Day 1 of each cycle up to the 30-day follow-up after last dose visit |
| Exploratory | Overall Survival | Time from C1D1 to death due to any reason | From enrollment to 12 months after the End of Treatment visit |
| | Treatment-related symptoms from the subject's perspective | Assessment of the five selected treatment-related symptoms from the subject's perspective (diarrhea, nausea, vomiting, dizziness, headache) using the PRO-CTCAE | From C1D1 to Day 1 of each cycle, at the End of Treatment visit up to the 30-Day Follow-up after last dose visit |
| | Prognostic markers | Genetic alterations, including cytogenetics and gene mutations in peripheral blood | From C1D1 to End of Treatment visit |
| | Mechanism of Action | Circulating proteins, including cytokines, immune and hematopoietic markers | From C1D1 to End of Treatment visit |

AEs = adverse events; C1D1 = Cycle 1 Day 1; CTC = Common Terminology Criteria for Adverse Events; ICF = informed consent form; MFSAF = Myelofibrosis Symptom Assessment Form; MRI = magnetic resonance imaging; NCI = National Cancer Institute; PRO-CTCAE = Patient Reported Outcome Version of Common Terminology Criteria of Adverse Events; SVR = spleen volume reduction.

Survival Follow-up Phase. All subjects discontinued from protocol-prescribed therapy for any reason will be followed for survival, subsequent therapies, new malignancy and progression of myelofibrosis to acute myeloid leukemia (AML) every 3 months until death or up to 12 months after end of treatment (EOT), lost to follow-up, withdrawal of consent for further data collection, or study closure.

The invention claimed is:

1. A method for treating a patient comprising:
   administering to the patient Compound I

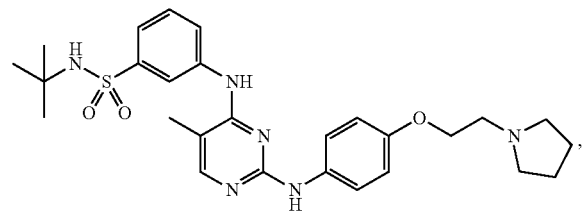

or a pharmaceutically acceptable salt and/or hydrate thereof;
   (ii) monitoring thiamine level in the patient; and
   (iii) administering to the patient thiamine or a thiamine equivalent if the patient's thiamine level is below a reference standard, wherein the reference standard is from about 74 to about 222 nM/L of whole blood wherein the patient has a myeloproliferative disorder.

2. The method of claim 1, wherein the patient's thiamine level is monitored by analyzing one or more biomarkers for thiamine deficiency.

3. The method of claim 1, wherein thiamine is administered to the patient at an amount of about 100 mg per day.

4. The method of claim 1, wherein thiamine is administered to the patient at an amount of about 250 mg to about 500 mg.

5. The method of claim 4, wherein thiamine is administered to the patient at an amount of about 250 mg.

6. The method of claim 4, wherein thiamine is administered to the patient at an amount of about 500 mg.

7. The method of claim 1, wherein thiamine is administered intravenously.

8. The method of claim 1, wherein thiamine is administered according to the following schedule:
   about 500 mg TID for 2 or 3 days;
   about 250 mg to about 500 mg daily (QD) for 3-5 days; and
   about 100 mg QD for 90 days.

9. The method of claim 1, wherein the patient is administered a thiamine equivalent sufficient to deliver about 100 mg of thiamine mg per day.

10. The method of claim 1, wherein thiamine or a thiamine equivalent is administered orally.

11. The method of claim 1, wherein the patient is administered a thiamine equivalent sufficient to deliver about 250 mg to about 500 mg of thiamine.

12. The method of claim 11, wherein the thiamine equivalent is sufficient to deliver about 250 mg of thiamine.

13. The method of claim 11, wherein the thiamine equivalent is sufficient to deliver about 500 mg of thiamine.

14. The method of claim 11, wherein the thiamine equivalent is sufficient to deliver an amount of thiamine according to the following schedule:
   about 500 mg TID for 2 or 3 days;
   about 250 mg to about 500 mg daily (QD) for 3-5 days; and
   about 100 mg QD for 90 days.

15. The method of claim 1, further comprising increasing the patient's magnesium level.

16. The method of claim 1, wherein the myeloproliferative disorder is myelofibrosis.

17. The method of claim 16, wherein the myelofibrosis is primary myelofibrosis.

18. The method of claim 17, wherein the primary myelofibrosis is selected from intermediate risk primary myelofibrosis and high risk primary myelofibrosis.

19. The method of claim 16, wherein the myelofibrosis is secondary myelofibrosis.

20. The method of claim 16, wherein the myelofibrosis is post essential thrombocythemia myelofibrosis.

21. The method of claim 16, wherein the myelofibrosis is post polycythemia vera myelofibrosis.

22. The method of claim 1, wherein the myeloproliferative disorder is acute myeloid leukemia (AML).

23. The method of claim 1, wherein the myeloproliferative disorder is polycythemia vera.

24. The method of claim 1, wherein the myeloproliferative disorder is essential thrombocythemia.

25. The method of claim 1, wherein Compound I is in the form of a dihydrochloride monohydrate salt.

* * * * *